(12) United States Patent
Duindam et al.

(10) Patent No.: US 11,737,682 B2
(45) Date of Patent: *Aug. 29, 2023

(54) SYSTEMS AND METHODS FOR REGISTRATION OF A MEDICAL DEVICE USING A REDUCED SEARCH SPACE

(71) Applicant: INTUITIVE SURGICAL OPERATIONS, INC., Sunnyvale, CA (US)

(72) Inventors: Vincent Duindam, San Francisco, CA (US); Prashant Chopra, Foster City, CA (US)

(73) Assignee: INTUITIVE SURGICAL OPERATIONS, INC, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/590,667

(22) Filed: Feb. 1, 2022

(65) Prior Publication Data
US 2022/0151508 A1 May 19, 2022

Related U.S. Application Data

(60) Continuation of application No. 16/402,531, filed on May 3, 2019, now Pat. No. 11,266,327, which is a (Continued)

(51) Int. Cl.
*A61B 34/20* (2016.01)
*A61B 5/06* (2006.01)
(Continued)

(52) U.S. Cl.
CPC ............... *A61B 5/066* (2013.01); *A61B 5/00* (2013.01); *A61B 5/061* (2013.01); *A61B 5/065* (2013.01);
(Continued)

(58) Field of Classification Search
CPC ........... A61B 5/066; A61B 5/00; A61B 5/061; A61B 5/065; A61B 34/10; A61B 34/20;
(Continued)

(56) References Cited

U.S. PATENT DOCUMENTS 5,920,319 A 7/1999 Vining et al.
6,380,732 B1 4/2002 Gilboa
(Continued)

FOREIGN PATENT DOCUMENTS

CN 1612708 A 5/2005
CN 1658789 A 8/2005
(Continued)

OTHER PUBLICATIONS

Extended European Search Report for Application No. 13791626.8, dated Jul. 15, 2016, 7 pages.
(Continued)

*Primary Examiner* — Rochelle D Turchen
(74) *Attorney, Agent, or Firm* — Haynes and Boone, LLP

(57) ABSTRACT

A medical system includes an elongate instrument, a tracking system, and one or more processors configured to: receive image data of a set of connected passageways of a patient anatomy; model the set as a plurality of linked bounded-surface elements, each linked bounded-surface element defined in part by basepoints on an anatomical centerline, an element centerline spanning a shortest distance between the basepoints, and a radius; receive position information for a point on the instrument when disposed in the set; based on a comparison of the received position information to the plurality of linked bounded-surface elements, generate adjusted position information for the point; match one of the plurality of linked bounded-surface elements to the point to register the instrument to the image data; create an adjusted instrument image with the adjusted position
(Continued)

information; and generate a composite image including the image data of the set and the adjusted instrument image.

19 Claims, 6 Drawing Sheets

Related U.S. Application Data division of application No. 13/892,871, filed on May 13, 2013, now Pat. No. 10,299,698.

(60) Provisional application No. 61/646,654, filed on May 14, 2012.

(51) Int. Cl.
| | |
|---|---|
| *G06T 7/00* | (2017.01) |
| *A61B 34/30* | (2016.01) |
| *A61B 34/10* | (2016.01) |
| *A61B 5/00* | (2006.01) |
| *A61B 90/00* | (2016.01) |
| *A61B 17/00* | (2006.01) |

(52) U.S. Cl.
CPC .............. *A61B 34/10* (2016.02); *A61B 34/20* (2016.02); *A61B 34/30* (2016.02); *G06T 7/0012* (2013.01); *A61B 2017/00809* (2013.01); *A61B 2034/108* (2016.02); *A61B 2034/2051* (2016.02); *A61B 2034/2061* (2016.02); *A61B 2034/301* (2016.02); *A61B 2090/365* (2016.02)

(58) Field of Classification Search
CPC .......... A61B 34/30; A61B 2017/00809; G06T 7/0012
See application file for complete search history.

(56) References Cited

U.S. PATENT DOCUMENTS

| | | | |
|---|---|---|---|
| 6,389,187 | B1 | 5/2002 | Greenaway et al. |
| 7,901,348 | B2 | 3/2011 | Soper et al. |
| 7,930,065 | B2 | 4/2011 | Larkin et al. |
| 10,039,473 | B2 | 8/2018 | Zhao et al. |
| 10,154,800 | B2 | 12/2018 | Duindam et al. |
| 10,299,698 | B2 | 5/2019 | Duindam et al. |
| 2003/0015207 | A1 | 1/2003 | Herold et al. |
| 2004/0249267 | A1 | 12/2004 | Gilboa et al. |
| 2005/0143651 | A1* | 6/2005 | Verard ................... A61B 34/20 |
| | | | 600/424 |
| 2006/0013523 | A1 | 1/2006 | Childlers et al. |
| 2006/0062447 | A1 | 3/2006 | Rinck et al. |
| 2006/0069317 | A1 | 3/2006 | Horn et al. |
| 2006/0149134 | A1 | 7/2006 | Soper et al. |
| 2006/0184016 | A1 | 8/2006 | Glossop |
| 2007/0001879 | A1 | 1/2007 | Kaftan et al. |
| 2007/0142749 | A1 | 6/2007 | Khatib et al. |
| 2007/0274579 | A1* | 11/2007 | Cai ...................... A61B 6/5211 |
| | | | 382/131 |
| 2007/0297561 | A1* | 12/2007 | Breeuwer ................. G06T 7/12 |
| | | | 382/169 |
| 2009/0209817 | A1 | 8/2009 | Averbuch |
| 2009/0227861 | A1* | 9/2009 | Ganatra ................. A61B 34/20 |
| | | | 600/424 |
| 2009/0268955 | A1 | 10/2009 | Koolwal et al. |
| 2009/0292166 | A1 | 11/2009 | Ito et al. |
| 2010/0016658 | A1* | 1/2010 | Zou ........................ G06T 17/10 |
| | | | 600/101 |
| 2011/0093243 | A1* | 4/2011 | Tawhai ................. G06T 7/0012 |
| | | | 703/2 |
| 2011/0103665 | A1* | 5/2011 | Gulsun .................. G06T 7/248 |
| | | | 382/131 |
| 2011/0224542 | A1* | 9/2011 | Mittal ..................... G06T 7/143 |
| | | | 600/425 |
| 2012/0029339 | A1 | 2/2012 | Cohen et al. |
| 2012/0069167 | A1 | 3/2012 | Liu et al. |
| 2012/0172761 | A1 | 7/2012 | Meller et al. |
| 2012/0289777 | A1* | 11/2012 | Chopra .............. A61B 1/00055 |
| | | | 382/128 |
| 2012/0289843 | A1 | 11/2012 | Chopra et al. |
| 2013/0094745 | A1 | 4/2013 | Sundar |
| 2013/0303891 | A1 | 11/2013 | Chopra |
| 2013/0303893 | A1 | 11/2013 | Duindam et al. |
| 2014/0235999 | A1 | 8/2014 | Birkenbach et al. |
| 2018/0325419 | A1 | 11/2018 | Zhao et al. |
| 2019/0175080 | A1 | 6/2019 | Duindam et al. |
| 2019/0320937 | A1 | 10/2019 | Duindam et al. |

FOREIGN PATENT DOCUMENTS

| | | | | |
|---|---|---|---|---|
| CN | 1874716 | A | | 12/2006 |
| CN | 101809618 | A | | 8/2010 |
| CN | 102428496 | A | | 4/2012 |
| CN | 102883651 | A | | 1/2013 |
| CN | 102949240 | A | | 3/2013 |
| EP | 2123216 | A1 | | 11/2009 |
| JP | 2008529641 | A | * | 2/2006 ............. G06T 7/149 |
| JP | 2007531543 | A | | 11/2007 |
| WO | WO-2005008591 | A2 | | 1/2005 |
| WO | WO-2006070669 | A1 | | 7/2006 |
| WO | WO-2007129616 | A1 | | 11/2007 |
| WO | WO-2009064715 | A1 | | 5/2009 |
| WO | WO-2011102012 | A1 | | 8/2011 |
| WO | WO-2012035492 | A1 | | 3/2012 |

OTHER PUBLICATIONS

Extended European Search Report for Application No. 19164298.2 dated Jul. 16, 2019, 8 pages.
International Search Report and Written Opinion for Application No. PCT/US2013/040775, dated Aug. 12, 2013, 12 pages.
LAN/MAN Standards Committee, "Part 11: Wireless LAN Medium Access Control (MAC) and Physical Layer (PHY) Specifications," IEEE Standard for Information technology, Telecommunications and Information Exchange Between Systems, Local and Metropolitan Area Networks, Specific Requirements, IEEE Std 802.11-2012 (Revision of IEEE Std 802.11-2007), IEEE Computer Society, Mar. 29, 2012, 2793 pages.
U.S. Appl. No. 60/588,336, inventor Childers: Brooks A., filed Jul. 16, 2004.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages, Dec. 22, 2022.

* cited by examiner

SYSTEMS AND METHODS FOR REGISTRATION OF A MEDICAL DEVICE USING A REDUCED SEARCH SPACE

CROSS-REFERENCE TO RELATED APPLICATIONS

This application is a continuation of U.S. patent application Ser. No. 16/402,531 filed May 3, 2019, which is a divisional application of U.S. application Ser. No. 13/892,871, filed May 13, 2013, which claims the benefit of U.S. Provisional Application No. 61/646,654, filed May 14, 2012, all of which are incorporated by reference herein in their entireties.

FIELD

The present disclosure is directed to systems and methods for tracking a medical device within a patient anatomy during a medical procedure, and more particularly to systems and methods for efficiently tracking a medical device within a patient anatomy using a reduced search space.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created connected passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of position and shape sensors to more accurately describe the shape, pose, and location of the surgical instrument in real space or with respect to pre-procedural or concurrent images. In a dynamic anatomical system and/or in an anatomical region dense with many anatomical passageways, accurately registering a minimally invasive instrument to the anatomical system is a time consuming and computer processing intensive task. Improved systems and methods are needed for increasing the accuracy and efficiency of systems and methods of registering minimally invasive instruments to the anatomical system.

SUMMARY

The embodiments of the invention are summarized by the claims that follow below.

In one embodiment, a method comprises identifying connected anatomical structures in stored images of a patient anatomy and generating a plurality of linkage elements representing the connected anatomical structures. The method also comprises receiving tracking data corresponding to a point on an instrument positioned within at least one of the connected anatomical structures; and matching the point on the instrument to one of the plurality of linkage elements.

In another embodiment, a medical system comprises a flexible instrument including a sensor adapted to provide tracking data for a point on the instrument and a memory storing images of a patient anatomy. The system also comprises a processor that identifies connected anatomical structures in the stored images of the patient anatomy and generates a plurality of linkage elements representing the connected anatomical structures. The processor also receives the tracking data corresponding to the point on an instrument positioned within at least one of the connected anatomical structures and matches the point on the instrument to one of the plurality of linkage elements.

In another embodiment, a method comprises generating an image of a set of connected passageways of a patient anatomy and receiving position information for a point on an instrument indicating a position of the point relative to the connected passageways. The method also includes generating adjusted position information for the point including modeling the set of connected passageways of a patient anatomy as a structure of linked cylinders and creating an adjusted instrument image with the adjusted position information. The method also includes generating a composite image including the image of the set of connected passageways and the adjusted instrument image.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the embodiments of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X,Y,Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
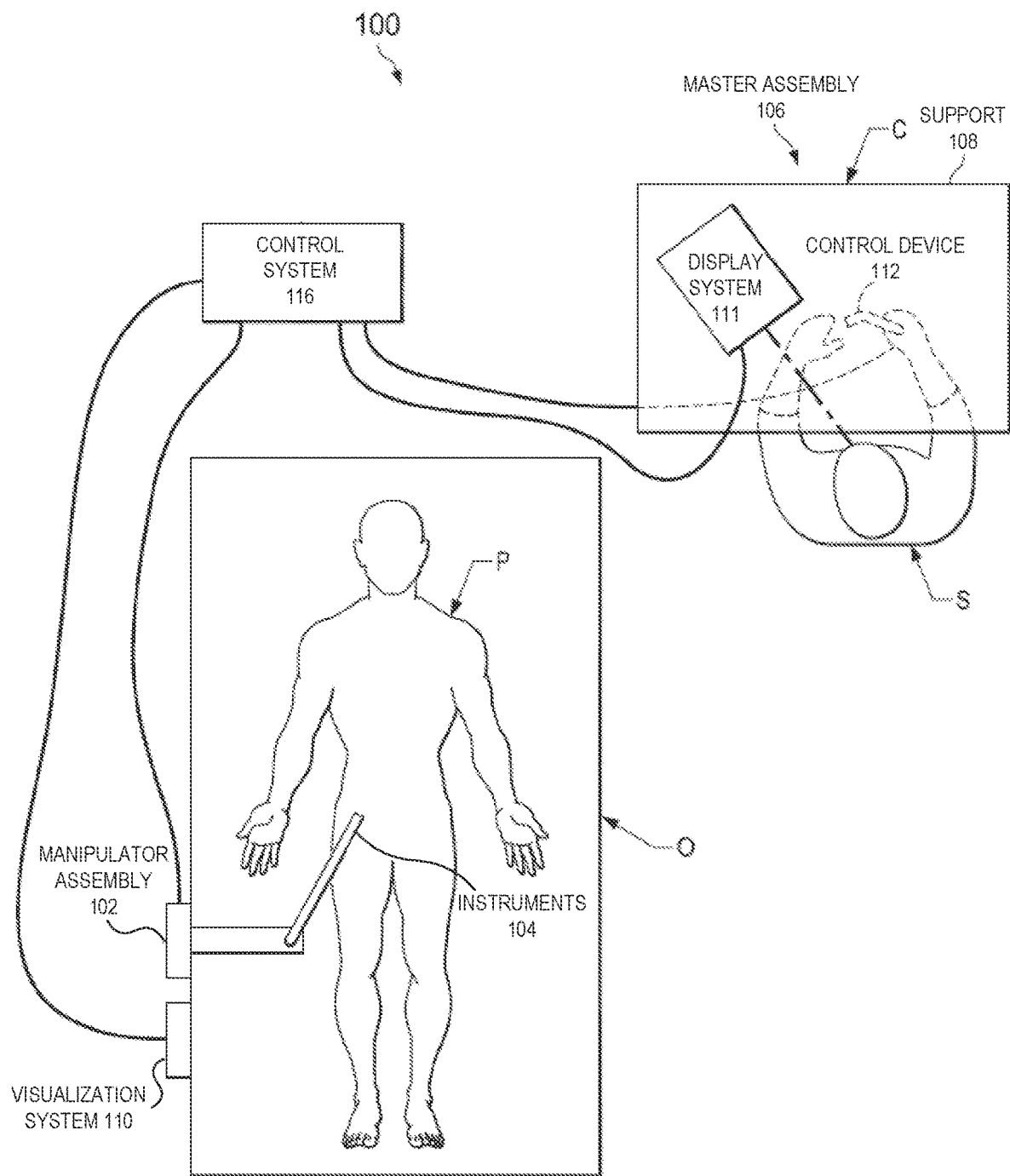
FIG. 1 is a robotic surgical system, in accordance with embodiments of the present disclosure.

Referring to FIG. 1 of the drawings, a robotic surgical system is generally indicated by the reference numeral 100. As shown in FIG. 1, the robotic system 100 generally includes a surgical manipulator assembly 102 for operating a surgical instrument 104 in performing various procedures on the patient P. The assembly 102 is mounted to or near an operating table O. A master assembly 106 allows the surgeon S to view the surgical site and to control the manipulator assembly 102.

In alternative embodiments, the robotic system may include more than one manipulator assembly. The exact number of manipulator assemblies will depend on the surgical procedure and the space constraints within the operating room among other factors.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the surgeon with telepresence, or the perception that the control device(s) 112 are integral with the instruments 104 so that the surgeon has a strong sense of directly controlling instruments 104. In some embodiments, the control devices 112 are manual input devices which move with six degrees of freedom, and which may also include an actuatable handle for actuating instruments (for example, for closing grasping jaws, applying an electrical potential to an electrode, delivering a medicinal treatment, or the like).

A visualization system 110 may include a viewing scope assembly (described in greater detail below) such that a concurrent or real-time image of the surgical site is provided to surgeon console C. The concurrent image may be, for example, a two or three dimensional image captured by an endoscope positioned within the surgical site. In this embodiment, the visualization system 100 includes endoscopic components that may be integrally or removably coupled to the surgical instrument 104. However in alternative embodiments, a separate endoscope, attached to a separate manipulator assembly may be used with the surgical instrument to image the surgical site. The visualization system 110 may be implemented as hardware, firmware, software or a combination thereof which interact with or are otherwise executed by one or more computer processors, which may include the processors of a control system 116 (described below).

A display system 111 may display an image of the surgical site and surgical instruments captured by the visualization system 110. The display 111 and the master control devices 112 may be oriented such that the relative positions of the imaging device in the scope assembly and the surgical instruments are similar to the relative positions of the surgeon's eyes and hands so the operator can manipulate the surgical instrument 104 and the hand control as if viewing the workspace in substantially true presence. By true presence, it is meant that the presentation of an image is a true perspective image simulating the viewpoint of an operator that is physically manipulating the surgical instruments 104.

Alternatively or additionally, monitor 111 may present images of the surgical site recorded and/or modeled preoperatively using imaging technology such as, computerized tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images.

In some embodiments, the monitor 111 may display a virtual navigational image in which the actual location of the surgical instrument is registered (i.e., dynamically referenced) with preoperative or concurrent images to present the surgeon S with a virtual image of the internal surgical site at the location of the tip of the surgical instrument. An image of the tip of the surgical instrument or other graphical or alphanumeric indicators may be superimposed on the virtual image to assist the surgeon controlling the surgical instrument. Alternatively, the surgical instrument may not be visible in the virtual image.

In other embodiments, the monitor 111 may display a virtual navigational image in which the actual location of the surgical instrument is registered with preoperative or concurrent images to present the surgeon S with a virtual image of surgical instrument within the surgical site from an external viewpoint. An image of a portion of the surgical instrument or other graphical or alphanumeric indicators may be superimposed on the virtual image to assist the surgeon controlling the surgical instrument.

As shown in FIG. 1, a control system 116 includes at least one processor and typically a plurality of processors for effecting control between the surgical manipulator assembly 102, the master assembly 106, and the image and display system 110. The control system 116 also includes software programming instructions to implement some or all of the methods described herein. While control system 116 is shown as a single block in the simplified schematic of FIG. 1, the system may comprise a number of data processing circuits (e.g., on the surgical manipulator assembly 102 and/or on the master assembly 106), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instruments 104 to the hand-operated control device 112. Any suitable conventional or specialized servo controller may be used. A servo controller may be separate from, or integral with manipulator assemblies 102. In some embodiments, the servo controller and manipulator assembly are provided as part of a robotic arm cart positioned adjacent to the patient's body. The servo controller transmits signals instructing the manipulator assemblies to move instruments which extend into an internal surgical site within the patient body via openings in the body.

Each of the manipulator assemblies 102 that support a surgical instrument 104 and may comprise a series of manually articulatable linkages, generally referred to as set-up joints, and a robotic manipulator. The robotic manipulator assemblies 102 may be driven by a series of actuators (e.g., motors). These motors actively move the robotic manipulators in response to commands from the control system 116. The motors are further coupled to the surgical instrument so as to advance the surgical instrument into a naturally or surgically created anatomical orifice and to move the distal end of the surgical instrument in multiple degrees of freedom that may include three degrees of linear motion (e.g., X,Y, Z linear motion) and three degrees of rotational motion (e.g., roll, pitch, yaw). Additionally, the motors can be used to actuate an articulatable end effector of the instrument for grasping tissues in the jaws of a biopsy device or the like.

Figure 2:
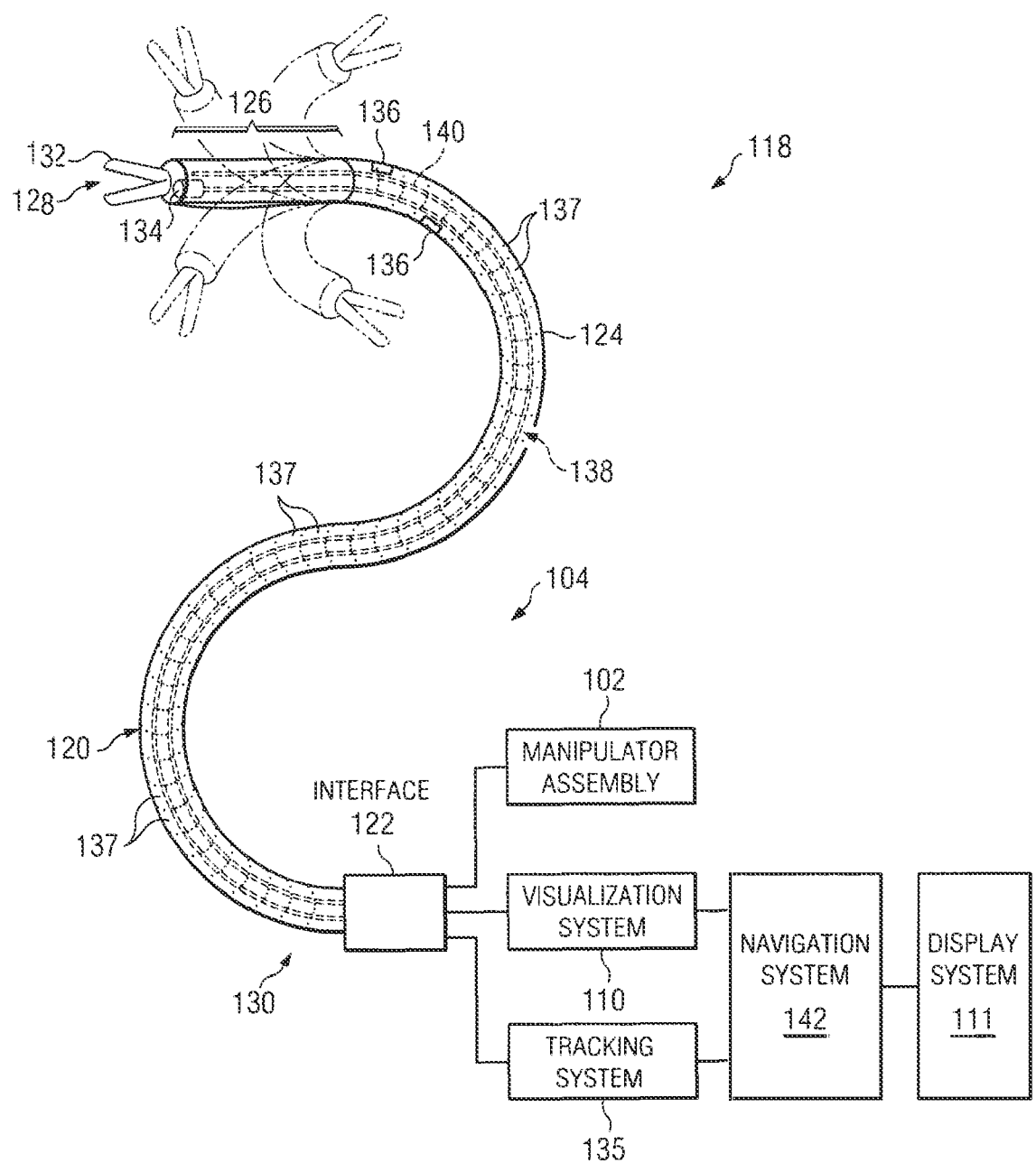
FIG. 2 illustrates a surgical instrument system utilizing aspects of the present disclosure.

FIG. 2 illustrates a tracked instrument system 118 which includes the surgical instrument system 104 and its interfacing systems. The surgical instrument system 104 includes a flexible instrument 120 coupled by an interface 122 to manipulator assembly 102 and visualization system 110. The instrument 120 has a flexible body 124, a tip 126 at its distal end 128, and the interface 122 at its proximal end 130. The body 124 houses cables, linkages, or other steering controls (not shown) that extend between the interface 122 and the tip 126 to controllably bend or turn the tip as shown for example by the dotted line versions of the bent tip 126, and in some embodiments control an optional end effector 132. The flexible instrument may be steerable, including the steering controls previously described, or may be non-steerable with no integrated mechanism for operator control of the instrument bending. The end effector may be a working distal part that is manipulable for a medical function, e.g., for effecting a predetermined treatment of a target tissue. For instance, some end effectors have a single working member such as a scalpel, a blade, or an electrode. Other end effectors such as shown in the embodiment of FIG. 2, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, treatments requiring fluid delivery, accessory introduction, biopsy extraction and the like). In other embodiments, flexible body 124 can define one or more lumens through which surgical instruments can be deployed and used at a target surgical location.

The instrument 120 can also include an image capture element 134 which may include a stereoscopic or monoscopic camera disposed at the distal end 128 for capturing images that are transmitted to and processed by the visualization system 110 for display by the display system 111. Alternatively, the image capture element 134 may be a coherent fiber-optic bundle that couples to an imaging and processing system on the proximal end of the instrument 120, such as a fiberscope. The image capture element 134 may be single or multi-spectral for capturing image data in the visible or infrared/ultraviolet spectrum.

A tracking system 135 includes an electromagnetic (EM) sensor system 136 and a shape sensor system 138 for determining the position, orientation, speed, pose, and/or shape of the distal end 128 and of one or more segments 137 along the instrument 120. The tracking system may also be used for registering the stored images of the patient anatomy and the shape sensor in a reference frame fixed to the patient. Registration may, alternatively, be performed using other techniques that do not utilize the EM sensor system, as would be understood by a person of ordinary skill in the art. Although only an exemplary set of segments 137 are depicted in FIG. 2, the entire length of the instrument 120, between the distal end 128 and the proximal end 130 and including the tip 126 may be effectively divided into segments. The tracking system 135 may be implemented as hardware, firmware, software or a combination thereof which interact with or are otherwise executed by one or more computer processors, which may include the processors of a control system 116.

The EM sensor system 136 includes one or more conductive coils that may be subjected to an externally generated electromagnetic field. Each coil of the EM sensor system 136 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 μm. In other embodiments, the dimensions may be larger or smaller.

The optical fiber 140 forms a fiber optic bend sensor for determining the shape of the instrument 120. In one alternative, optical fibers including Fiber Bragg Gratings (FBGs) are used to provide strain measurements in structures in one or more dimensions. Various systems and methods for monitoring the shape and relative position of a optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the instrument 120 may be determined using other techniques. For example, if the history of instrument tip's pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the instrument. Alternatively, a series of positional sensors, such as EM sensors, positioned along the instrument can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding 146. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber 140 is used to monitor the shape of at least a portion of the instrument 120. More specifically, light passing through the optical fiber 140 is processed by the tracking system 135 for detecting the shape of the surgical instrument 120 and for utilizing that information to assist in surgical procedures. The tracking system 135 may include a detection system for generating and detecting the light used for determining the shape of the instrument 120. This information, in turn, in can be used to determine other related variables, such as velocity and acceleration of the parts of a surgical instrument. By obtaining accurate measurements of one or more of these variables in real time, the controller can improve the accuracy of the robotic surgical system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images to provide the surgeon or other operator with real-time position information on the display system 111 for use in the control of the instrument 120. The control system 116 may utilize the position information as feedback for positioning the instrument 120. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 104 is teleoperated within the robotic surgical system 100. In an alternative embodiment, the manipulator assembly may be replaced by direct operator control. In the direct operation alternative, various handles and operator interfaces may be included for hand-held operation of the instrument.

Figure 3B:
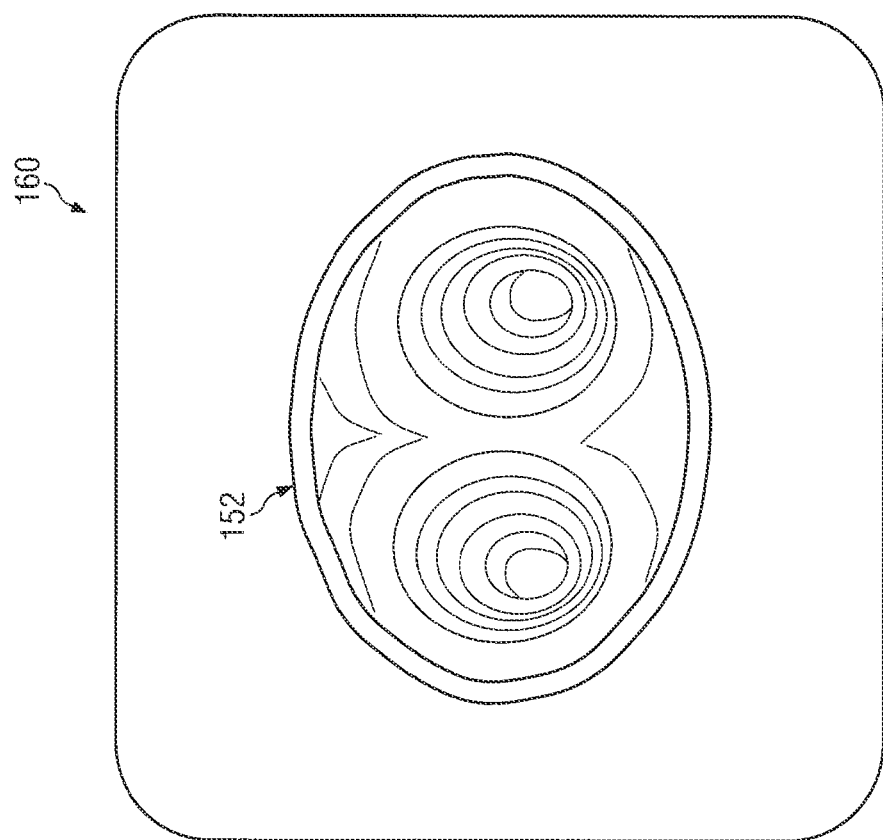
FIG. 3b is an internal image of the human lung depicting the region of the human lung from the viewpoint of the minimally invasive instrument.
Figure 3A:
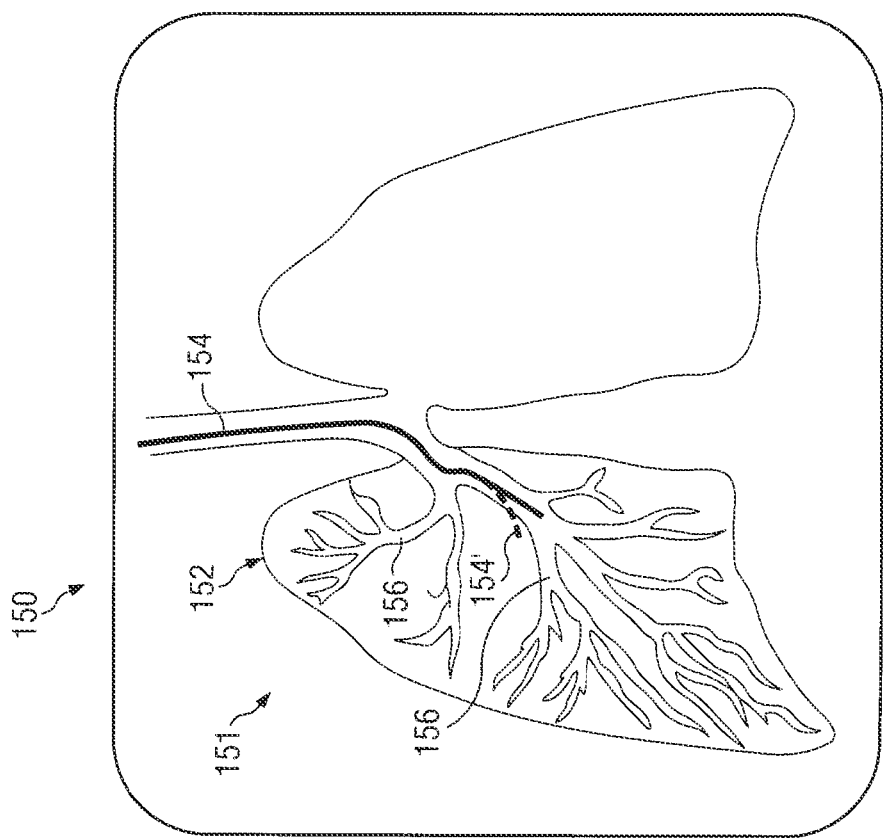
FIG. 3a is an image of a human lung registered with an image of a minimally invasive instrument.

FIG. 3a depicts a composite image 150 including an image 151 of a human lung 152, from a viewpoint external to the lung, registered with an instrument image 154 of a flexible instrument, such as the flexible instrument 120. The image 151 of the lung 152 may be generated from preoperatively recorded images or may be generated concurrently during the surgical procedure. The composite image 150 may be displayed via display system 111. As the instrument 120 is advanced through bronchial passageways 156 of the lung 152, information from the tracking system 135 and/or the visualization system 110 are used to register the instrument image 154 with the lung image 151. The image 151 of the lung 152 may change, for example, to depict the lung in a state of inspiration or expiration. The instrument image 154 may change to depict the advancement or withdrawal of the instrument 120 through the bronchial passageways 156. Occasionally, the composite image 150 may erroneously render the instrument image 154 such that a portion of the instrument image 154' is outside of a bronchial passageway. Systems and methods are described below for correcting the instrument image such that the instrument is located within the bronchial passageways.

FIG. 3b depicts an internal image 160 of the human lung 152 depicting a region of the lung from the viewpoint of the instrument 120. The image 160 may be a concurrent image taken during the surgical procedure by the instrument 120 while located in the depicted portion of the lung 152. More specifically, the image may be captured by the visualization system 110. Alternatively, the image 160 may be a preoperatively recorded image selected based upon the location of the tip of the instrument 120 as determined by the tracking system 135.

Often, the tracking system 135, which includes the EM sensor system 136 and the shape sensor system 138 may calculate a position for the instrument tip 126 or one or more segments 137 of the instrument 120 that is outside the anatomical passageway. This likely indicates a slight measurement error (assuming the wall of the anatomical passageway has not been breached). Such an error may result from the dynamic nature of certain anatomic structures such as the lungs or the heart. For example, inhalation and exhalation changes the position and size of the bronchial passageways of the lung. Alternatively, the error may result from tissue deformation caused by the presence of the surgical instrument within the anatomic passageways. To correct the position of the instrument and accurately locate one or more points of the instrument within the passageway when the image of the instrument and the image of the patient anatomy are co-registered and displayed, selected points of the instrument may be snapped or graphically registered to a location on the wall of the anatomical passageway or to the lumen of the anatomical passageway.

Figure 5:
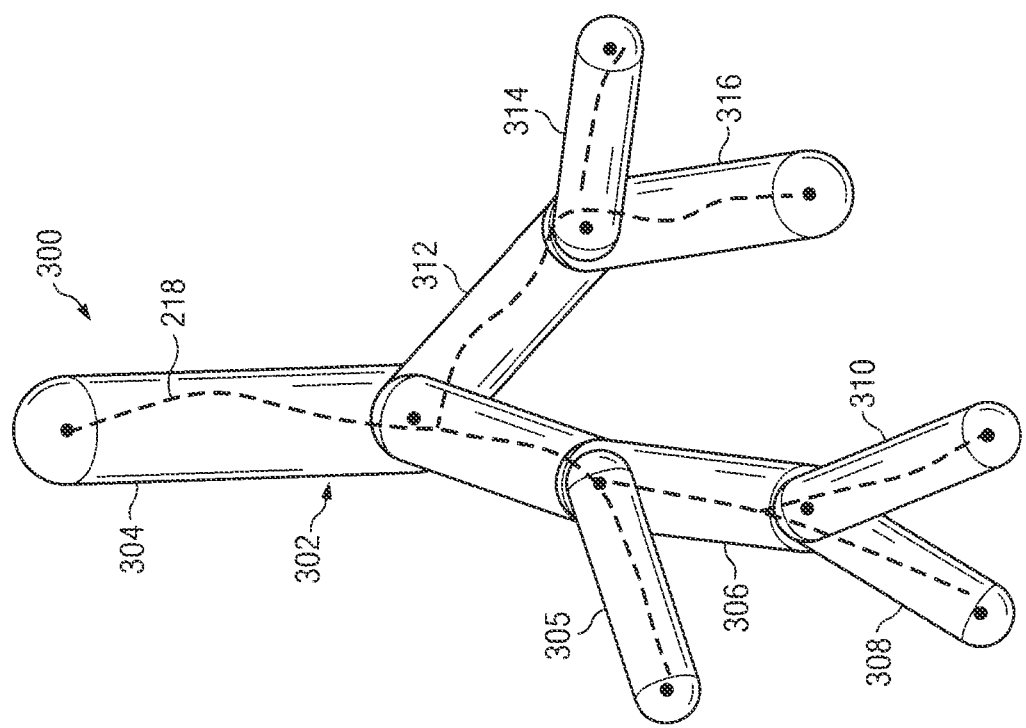
FIG. 5 is an illustration of a plurality of cylindrical linkage elements representing the bronchial passageway of FIG. 4.
Figure 4:
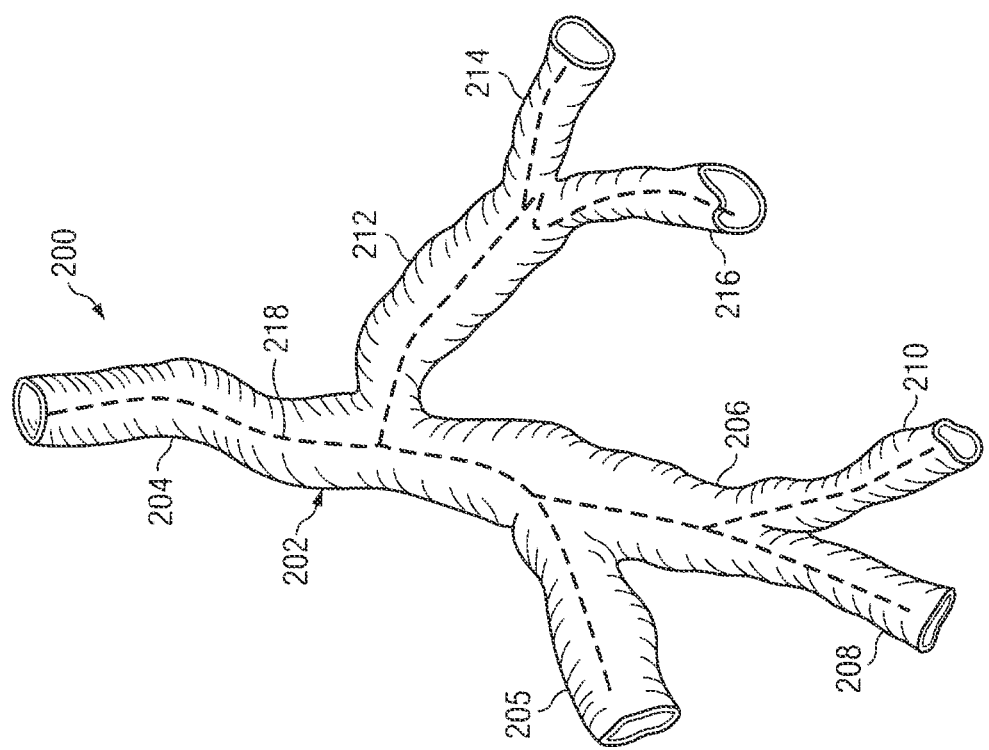
FIG. 4 is an illustration of a portion of bronchial passageway of a lung.

In one embodiment snapping a point on an instrument to an anatomical passageway begins by modeling a stored image of the anatomical passageway. FIG. 4 is a three dimensional model 200 of a portion of bronchial structure 202 of a lung as captured in preoperative image. The bronchial structure 202 includes discrete bronchial passageways 204-216. A series of centerpoints through the bronchial passageways 204-216 form the anatomic centerline 218. The image 200 may be a composite image formed from a plurality of preoperative images. FIG. 5 is an illustration 300 of a three dimensional linked structure 302 of cylindrical linkage elements 304-316 representing the bronchial passageways 204-216. As will be described in detail below, the connected cylindrical linkage elements 304-316 are determined from the anatomic centerline 218. Representing the bronchial structure 202 as the linked cylinder structure 302 may reduce the search space for determining the specific bronchial passageway in which an instrument point is located. Although reference is frequently made to branched anatomical passageways, the systems and embodiments of this application are also applicable to modeling a single passageway as a series of joined cylinders. This may be particularly useful if the passageway is curved or varies in diameter along its length.

Figure 6:
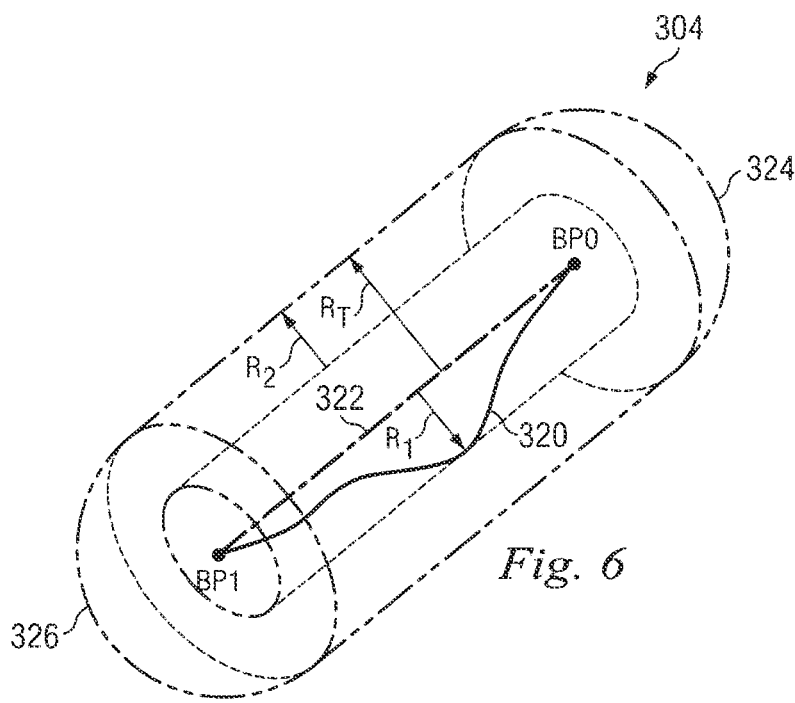
FIG. 6 is an illustration of a cylindrical linkage element.

FIG. 6 is an illustration of the cylindrical linkage element 304. The cylindrical linkage element 304 is formed about a branch 320 of anatomic centerline 218. The branch 320 includes a base point BP0 and a base point BP1 at opposite ends of the branch. A cylindrical centerline 322 spans the shortest distance between the base point BP0 and the base point BP1. The total radius $R_T$ of the cylindrical linkage element 304 can be the combined length of radius $R_1$ and radius $R_2$. The radius $R_1$ is the maximum deviation between the anatomic centerline 218 and the cylindrical centerline 322. Thus, the larger the deviation between the centerlines, the larger the total cylinder radius approximation. The radius $R_2$ is the average radius of the bronchial passageway 204 as obtained, for example, from the model 200. In one embodiment, the cylindrical linkage element 304 can include spherically-shaped ends 324, 326. The overlapping spherically-shaped ends 324, 326 can simplify the computational burden associated with modeling linkage element 304, and can provide an intuitive "joint" element with adjacent linkage elements. However, in various other embodiments, cylindrical linkage element 304 can have ends of any configuration (e.g., flat, angled, faceted, or any other modeling configuration).

Note that in various other embodiments, the total radius $R_T$ can be defined in various alternative manners to provide a desired level of representation for branch 320. For example, in some embodiments, total radius $R_T$ can be simply be equivalent to the average radius of the bronchial passageway 204 (i.e., radius R2), the maximum radius of bronchial passageway 204, or any other appropriate characteristic of bronchial passageway 204. In other embodiments, radius $R_1$ (or any other adjustment factor such as a pre-determined "buffer" distance, or even a varying radius along cylindrical linkage element 304) can be added to any of the above bronchial passageway-related radii.

Figure 7:
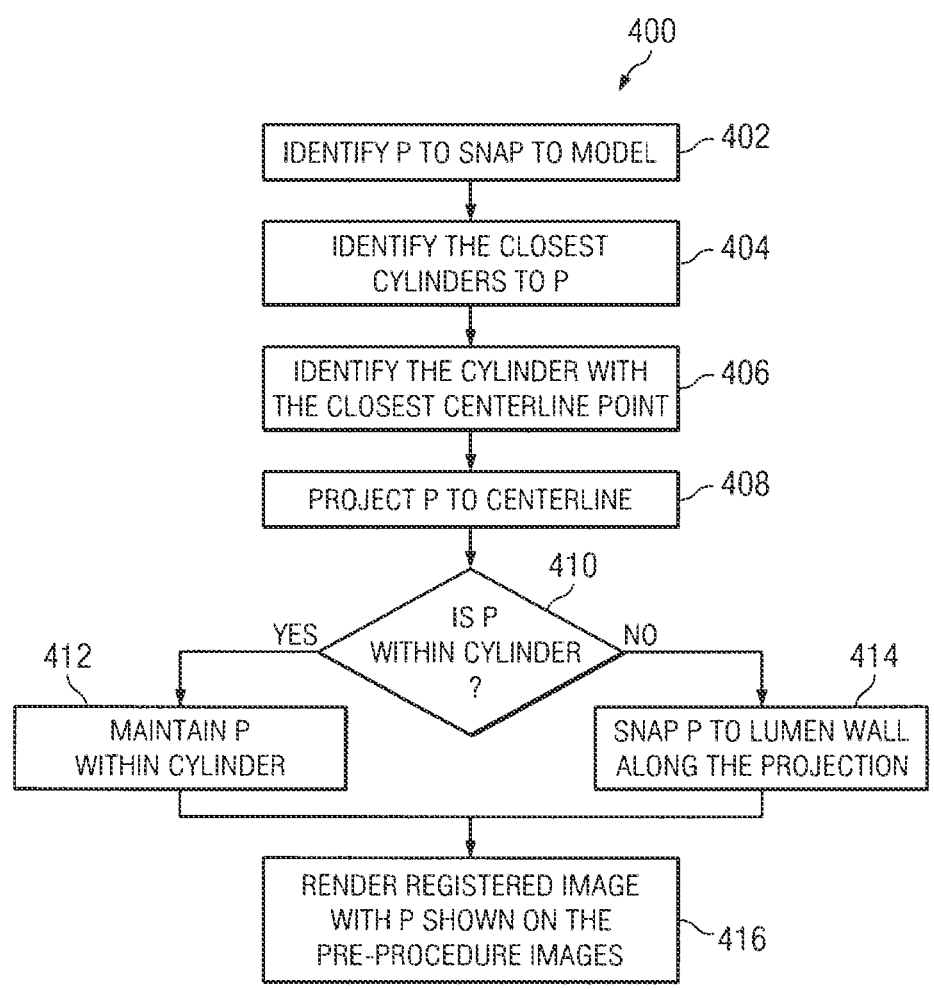
FIG. 7 is a flowchart illustrating a method for snapping a point of an instrument to an anatomical passageway.

FIG. 7 is a flowchart 400 illustrating a method for snapping a three dimensional point P of the instrument 154 to a bronchial passageway. This method may be used to correct the image of the instrument at point P when, for example as shown in FIG. 3a, the tracking system information, including information from a shape sensor and/or an EM sensor, positions a portion of the instrument, including point P, outside of a bronchial passageway. Initially, connected anatomical structures are identified in stored images of a patient anatomy. Connected anatomical structures include branching anatomical passageways, where each passageway is connected to at least one other passageway. A plurality of cylindrical linkage elements are generated to represent the connected anatomical structures, as described above.

At step 402, a point P is identified to be snapped to a bronchial passageway. The point P may have been identified as a point on a bronchial instrument that has been tracked to a location outside of a bronchial passageway. In some embodiments the point P may be a distal tip of the bronchial instrument, but in alternative embodiments the point P may be any point along the instrument within the bronchial passageway. At step 404, the closest of the cylindrical linkage elements 304-316 to point P are identified. For example, to determine the distance between the point P and each cylindrical linkage element 304-316, the general location of the point P relative to the cylindrical linkage element is first determined. The general location of the point P relative to each of the cylindrical linkage elements is considered because the distance to be calculated is the distance between the point P and the closest point on the cylindrical centerline of each element, including the base points BP0 and BP1.

Figure 8:
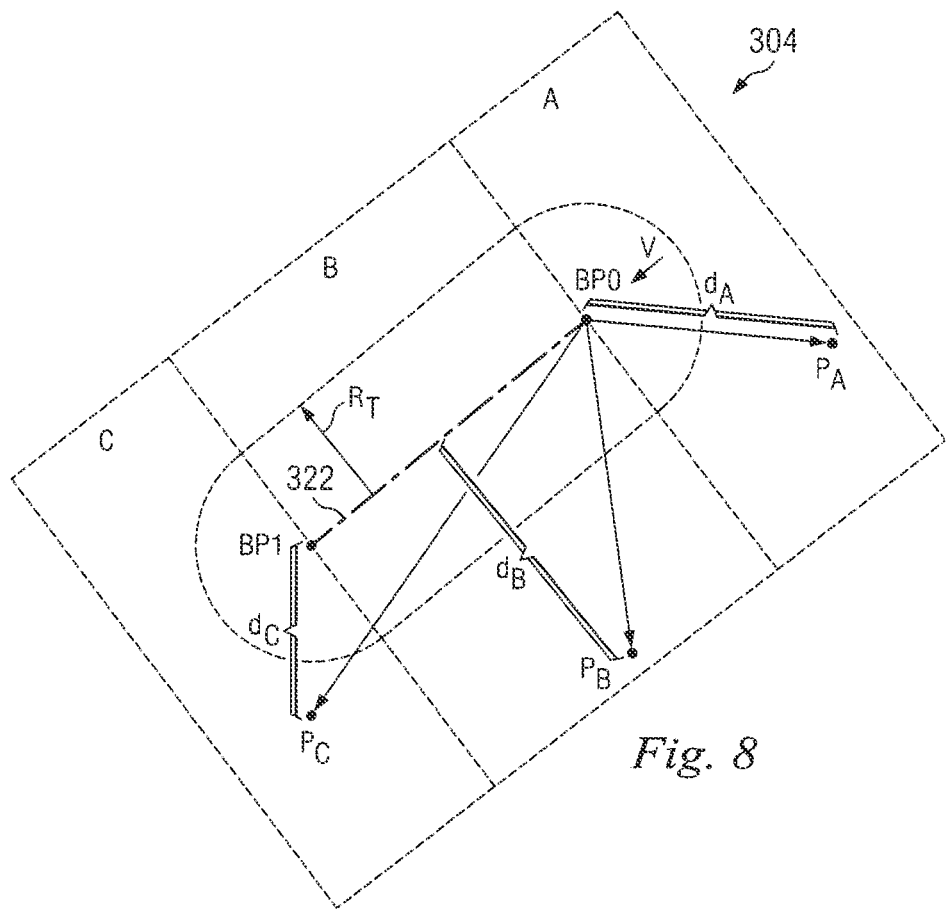
FIG. 8 is an illustration of a cylindrical linkage element.

With reference to FIG. 8, the point P may be in one of three locations relative to the cylindrical linkage element 304. First, the point P could be $P_A$, in the region A near BP0. Second, the point P could be $P_B$, in the region B between BP0 and BP1. Third, the point P could be $P_C$, in the region C near BP1. To determine the region in which point P is located, the inner product of the unit directional vector V from BP0 to BP1 and the vector from BP0 to P is calculated. If the inner product is less than zero, P is closest to BP0 (region A). If the inner product is between BP0 and BP1, P is closer to BP1 (region C). If the inner product is otherwise, P is somewhere at a midpoint between BP0 and BP1. After the location of the point P relative to the cylindrical linkage element 304 is determined, the distance from P to the closest point on the centerline 322 is calculated. This determination of point P location and distance is performed for each of the cylindrical linkage elements 304-316. The cylindrical linkage elements 304-316 with the shortest distances to P are considered the closest cylindrical linkage elements. Further processing is performed only on these closest cylindrical linkage elements. In one embodiment, the closest five cylindrical linkage elements may be chosen, but in other embodiments more or fewer elements may be suitable.

At step 406, for the closest cylindrical linkage elements to point P, a search is performed to identify the closest point on the anatomic centerline for each of the closest cylindrical linkage elements. After the closest point on the anatomic centerline is determined for each of the closes cylindrical linkage elements, the cylindrical linkage element with the closest overall anatomic centerline point $P_i$ is chosen.

Figure 9:
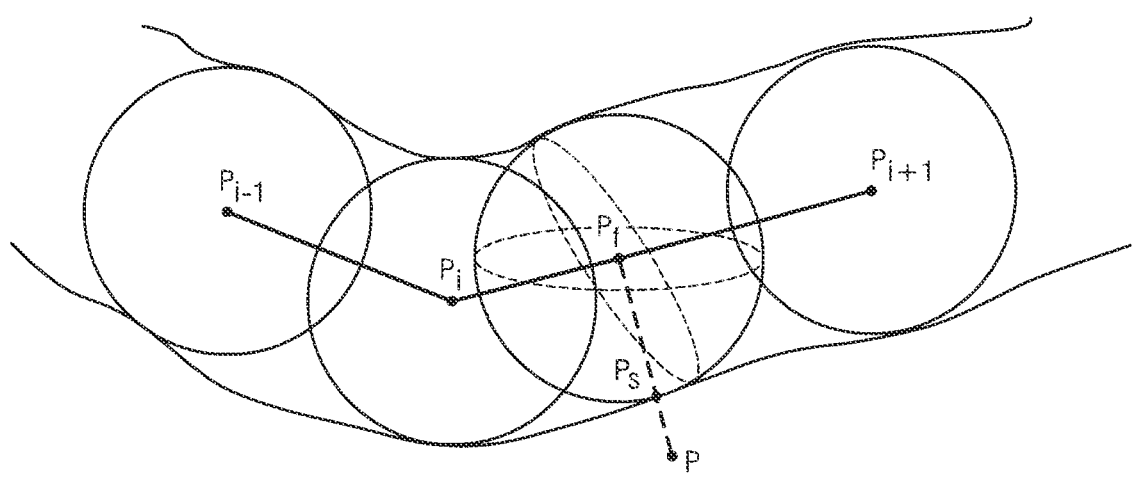
FIG. 9 is an illustration of an instrument point projected to a centerline of a cylindrical linkage element.

At step 408 and with reference to FIG. 9, a final point $P_f$ along the anatomic centerline of the closest cylindrical linkage element is determined. More specifically, refinement calculations are performed to determine if final point $P_f$ is between two centerline point $P_i$ and $P_{i+1}$ or between $P_i$ and $P_{i-1}$. After the final point $P_f$ is determined, the point P is projected along a straight line towards $P_f$ until it coincides with a sphere around $P_f$ with a radius approximately equal to the diameter of the bronchial passage at $P_f$. The point $P_S$ represents the position on the wall of the bronchial passageway to which the point P will be snapped.

At step 410, the point P is evaluated to determine whether it is outside a cylindrical linkage element or inside a cylindrical linkage element. If the point P is inside the cylindrical linkage element, at step 412, the rendered image of the point P on the instrument image is maintained within the bronchial passage on the co-registered lung image. If the point P is outside the cylindrical linkage element, at step 414, the rendered image of the point P on the instrument image is adjusted or snapped to the point $P_S$ along the projection between P and $P_f$ where the projection intersects the wall of the bronchial passage. At step 416, a corrected image composite image 150 depicting the image 151 of a human lung 152 registered with an corrected instrument image 154 is prepared. In the corrected images, the point P is snapped to the bronchial passageway rather than extending outside the bronchial wall.

The systems and methods described may conserve time and computer processing resources as compared to "brute-force" methods that attempt to directly snap a point P to the correct bronchial passageway by comprehensively considering each point along the wall of a bronchial passageway or at each point along a centerline of the bronchial passageway. For example, the time for the snapping procedure with the methods of this disclosure may be approximately 35 μs compared to 210 μs for the brute-force method.

Alternative systems and methods for registering an image of at least a portion of a flexible instrument to an image of an anatomical system are disclosed in U.S. Pat. App. No. (Ref. No. ISRG04300), disclosing "Systems and Methods for Deformation Compensation Using Shape Sensing" and in U.S. Pat. App. No. (Ref. No. ISRG03740), disclosing "Systems and Methods for Registration of a Medical Device Using Rapid Pose Search," both of which are incorporated by reference herein in their entirety. Aspects of theses incorporated by reference systems and methods may be used together with the above disclosed systems and methods to provide alternative methods of accurately registering an image of at least a portion of a flexible instrument to an image of an anatomical system.

Although the registration systems and methods have been described herein with respect to teleoperated or hand operated surgical systems, these registration systems and methods will find application in a variety of medical and non-medical instruments in which accurate instrument image registration is otherwise too time consuming or computer processing intensive.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

Although the embodiments described above use cylindrical linkages to model the anatomic structure, a person of skill in the art would know how to use additional bounding-surface linkages with well-defined surfaces, without departing from the spirit of the invention. For example, ellipsoidal, hyperbolic, spheroidal linkages could be used. In general, well-defined surfaces of bounding envelope type could be used for any of the embodiments above.

What is claimed is:

1. A medical system comprising:
an elongate instrument;
a tracking system disposed along at least a portion of the elongate instrument; and
one or more processors coupled to the tracking system, wherein the one or more processors are configured to:
receive image data of a set of connected passageways of a patient anatomy;
model the set of connected passageways of the patient anatomy as a plurality of linked bounded-surface elements, each of the plurality of linked bounded-surface elements defined in part by basepoints on an anatomical centerline, an element centerline spanning a shortest distance between the basepoints, and a radius;
receive position information for a point on the elongate instrument when the point is disposed in the set of connected passageways;
based on a comparison of the received position information to the plurality of linked bounded-surface elements, generate adjusted position information for the point on the elongate instrument;
match one of the plurality of linked bounded-surface elements to the point to register the elongate instrument with respect to the image data;
create an adjusted instrument image with the adjusted position information; and
generate a composite image including the image data of the set of connected passageways and the adjusted instrument image.

2. The medical system of claim 1, wherein the radius is at least partially based on an average radius of a corresponding passageway of the set of connected passageways.

3. The medical system of claim 2, wherein the radius is at least partially based on a deviation distance between the anatomical centerline and the element centerline.

4. The medical system of claim 3, wherein the deviation distance is a maximum deviation distance along the element centerline.

5. The medical system of claim 3, wherein the radius equals a sum of the average radius and the deviation distance.

6. The medical system of claim 1, wherein the radius is at least partially based on a maximum radius of a corresponding passageway of the set of connected passageways.

7. The medical system of claim 6, wherein the radius is at least partially based on a deviation distance between the anatomical centerline and the element centerline.

8. The medical system of claim 7, wherein the deviation distance comprises a maximum deviation distance along the element centerline.

9. The medical system of claim 7, wherein the radius equals a sum of the maximum radius and the deviation distance.

10. The medical system of claim 1, wherein each of the plurality of linked bounded-surface elements is further defined by opposing ends such that each of the plurality of linked bounded-surface elements forms an enclosed volume.

11. The medical system of claim 10, wherein the opposing ends are hemispherical.

12. The medical system of claim 1, wherein the image data includes preoperative images.

13. The medical system of claim 1, wherein generating adjusted position information for the point further includes changing the position information for the point on the elongate instrument to a location on a wall of the matched linked bounded-surface element.

14. The medical system of claim 1, wherein generating adjusted position information for the point includes determining a set of distances between the point on the elongate instrument and the element centerlines of a subset of the plurality of the linked bounded-surface elements.

15. The medical system of claim 14, wherein generating adjusted position information for the point further includes identifying a smallest distance from the set of distances and identifying the matched linked bounded-surface element based on the smallest distance.

16. The medical system of claim 1, wherein generating the adjusted position information for the point further includes generating a projection between the point on the elongate instrument and the element centerline of the matched linked bounded-surface element.

17. The medical system of claim 16, wherein the adjusted position information includes an adjusted position for the point on the elongate instrument that is along the projection at a wall of the matched linked bounded-surface element.

18. A medical system comprising:
an elongate instrument;
a tracking system disposed along at least a portion of the elongate instrument; and
one or more processors coupled to the tracking system, wherein the one or more processors are configured to:
receive position information for a point on the elongate instrument when the point is disposed in a set of connected passageways of a patient anatomy;
compare the received position information to a plurality of linked bounded-surface elements of a model of the set of connected passageways, wherein each of the plurality of linked bounded-surface elements is defined in part by basepoints on an anatomical centerline of the model, an element centerline spanning a shortest distance between the basepoints, and a radius;
generate adjusted position information for the point on the elongate instrument based on the comparing;
register the elongate instrument with respect to the model by matching one of the plurality of linked bounded-surface elements to the point;
create an adjusted instrument image with the adjusted position information; and
generate a composite image including the model of the set of connected passageways and the adjusted instrument image.

19. The medical system of claim 18, wherein the radius is at least partially based on an average radius of a corresponding passageway of the set of connected passageways.

* * * * *